United States Patent [19]

Hopp et al.

[11] Patent Number: 5,268,343

[45] Date of Patent: Dec. 7, 1993

[54] PROCESS FOR THE REACTIVATION OF AN ACTIVATED CHARCOAL CATALYST EMPLOYED IN THE PREPARATION OF 1,1,1,2,3,3,3-HEPTAFLUOROPROPANE (R 227)

[75] Inventors: Peter Hopp, Hofheim am Taunus; Uwe Wirth, Mainhausen, both of Fed. Rep. of Germany

[73] Assignee: Hoechst Aktiengesellschaft, Frankfurt am Main, Fed. Rep. of Germany

[21] Appl. No.: 36,803

[22] Filed: Mar. 25, 1993

[30] Foreign Application Priority Data

Mar. 26, 1992 [DE] Fed. Rep. of Germany ....... 4209800

[51] Int. Cl.$^5$ .................... B01J 37/34; B01J 21/18; B01J 38/02; C07C 17/08
[52] U.S. Cl. ............................................. 502/5; 502/34; 502/56; 570/165
[58] Field of Search ............... 502/5, 34, 56; 570/134, 570/165

[56] References Cited

U.S. PATENT DOCUMENTS

| | | | |
|---|---|---|---|
| 4,322,394 | 3/1982 | Mezey et al. | 502/5 |
| 5,087,778 | 2/1992 | Yates | 502/34 |

FOREIGN PATENT DOCUMENTS 902590  8/1962  United Kingdom .

OTHER PUBLICATIONS

*Ullmann's Encyclopedia of Industrial Chemistry*, ("Adsorption"), Fourth Ed., Band 2, 1972, pp. 610–613.

*Primary Examiner*—Paul E. Konopka

[57] ABSTRACT

The invention relates to a process for the reactivation of an activated charcoal catalyst employed in the preparation of 1,1,1,2,3,3,3-heptafluoropropane (R 227) in which the catalyst is heated to from 450° to 900° C. in a stream of inert gas or under reduced pressure.

6 Claims, No Drawings

PROCESS FOR THE REACTIVATION OF AN ACTIVATED CHARCOAL CATALYST EMPLOYED IN THE PREPARATION OF 1,1,1,2,3,3,3-HEPTAFLUOROPROPANE (R 227)

A substitute which has been proposed in some applications for the ozone-endangering fully halogenated chlorofluorocarbons is 1,1,1,2,3,3,3-heptafluoropropane (R 227). In the preparation thereof from hexafluoropropene and HF, the catalyst used is activated charcoal (British Patent 902,590). However, it has been found that the catalyst loses its activity after only a relatively short time. The loss in activity is evident, inter alia, from the fact that the hot spot, which, at the beginning of the reaction, is at the beginning of the catalyst bed (point of entry of hexafluoropropene and HF), gradually migrates to the end of the bed. At the same time, an increase in the weight of the activated charcoal is observed. The object was to develop a process which enables reactivation of the charcoal catalyst.

It has already been disclosed that, in the case of activated charcoal which has been used as an adsorbent, desorption of the adsorbed substances, and thus regeneration of the adsorbent, can sometimes be achieved by increasing the temperature (Ullmann's Encyclopedia, 4th Edition, Volume 2 (1972), pp. 610-613). In general, temperatures of from about 300° to 500° C. are used. However, if the adsorbate has low volatility, heating does not cause regeneration. Instead, the adsorbed organic impurities carbonize on heating and cause permanent damage. In this case, new adsorption pores can be created by treatment with $CO_2$- and steam-containing gas at about 900° C. However, this reactivation of the activated charcoal as adsorbent is associated with loss of charcoal, since a chemical reaction of the activated charcoal with the reactivation gas takes place (Ullman, loc. cit., in particular p. 612).

Surprisingly, it has now been found that activated charcoal which has been employed as catalyst in the preparation of R 227 and has thus lost some or all of its catalytic activity can be reactivated by heating to from 450° to 900° C. in a stream of inert gas or in vacuo. This is surprising since it would have been expected that the activated charcoal has been deactivated through adsorption of non-volatile oligomers, which would carbonize on heating to from 450° to 900° C.

The invention therefore relates to a process for the reactivation of an activated charcoal catalyst employed in the preparation of 1,1,1,2,3,3,3-heptafluoropropane (R 227), which comprises heating the catalyst to from 450° to 900° C. in a stream of inert gas or under reduced pressure.

It is preferred to carry out the process in a stream of inert gas. The preferred inert gas is nitrogen. The inert gas can be heated to from 450° to 900° C.; in this case, additional heating of the activated charcoal by other means is unnecessary, although possible. However, if the inert gas cannot itself be heated to from 450° to 900° C., the activated charcoal must be heated to said temperature by other means; it is preferably irradiated with microwaves. The stream of inert gas or the pressure reduction causes the gases formed on heating of the activated charcoal to be transported away.

The activated charcoal catalyst is preferably heated to from 550° to 800° C., in particular to from 600° to 800° C.

After treatment for from 1 to 24 hours, preferably for from 5 to 10 hours, the reactivation is complete. This treatment can be carried out within or outside the R 227 production plant. If heating is effected by microwaves, the reactivation proceeds particularly quickly, even at temperatures of from 450° to 650° C.

Essential completion of the reactivation can be detected from the fact that the hot spot has migrated back to the point of entry of hexafluoropropene and HF into the catalyst bed.

If the process is carried out under reduced pressure, this is preferably less than 1 mbar.

It is also possible to use superheated steam mixed with $CO_2$ at from 450° to 900° C.

The examples below serve to illustrate the invention.

EXAMPLE 1

30 g of activated charcoal which had been used as catalyst in the synthesis of R 227 from hexafluoropropene and HF and had thus substantially lost its activity were introduced into a tubular reactor made from quartz glass. The tubular reactor was introduced into a microwave apparatus. The activated charcoal in the reactor was irradiated for 20 minutes with microwaves at an output of 400 watts and at a frequency of 2450 MHz, during which the activated charcoal was heated to 600° C. During the heating, a 10 l/h stream of nitrogen was passed over the activated charcoal. It had subsequently recovered its full catalytic activity, which is evident from the position of the hot spot.

EXAMPLE 2

3 kg of activated charcoal which had been used in the synthesis of R 227 and had substantially lost its catalytic activity were heated to 300° C. over the course of 5 hours and to 550° C. over the course of a further 10 hours in an electrically heated furnace. This temperature was maintained for 9 hours. Over the entire time, the activated charcoal was flushed with 50 l/h of nitrogen. It had subsequently recovered its full catalytic activity.

We claim:

1. A process for the reactivation of an activated charcoal catalyst employed in the preparation of 1,1,1,2,3,3,3-heptafluoropropane (R 227), which comprises heating the catalyst to from 450° to 900° C. in a stream of inert gas or under reduced pressure.

2. The process as claimed in claim 1, wherein the catalyst is heated to from 550° to 800° C.

3. The process as claimed in claim 1, wherein the catalyst is heated to from 600° to 800° C.

4. The process as claimed in claim 1, wherein the catalyst is heated by microwave irradiation.

5. The process as claimed in claim 1, wherein the catalyst is heated in a stream of inert gas.

6. The process as claimed in claim 5, wherein the inert gas employed is nitrogen.

* * * * *